(12) United States Patent
Deppisch et al.

(10) Patent No.: US 6,841,255 B2
(45) Date of Patent: Jan. 11, 2005

(54) BIOCOMPATIBLE POLYMER FILM

(75) Inventors: Reinhold Deppisch, Hechingen (DE); Ulrich Bauer, Hechingen (DE); Werner Beck, Rottenburg (DE); Ruth Dietrich, Hechingen (DE); Hermann Göhl, Bisingen-Zimmern (DE); Katja Krämer, Reutlingen (DE)

(73) Assignee: Gambro AB, Stockholm (SE)

( * ) Notice: Subject to any disclaimer, the term of this patent is extended or adjusted under 35 U.S.C. 154(b) by 0 days.

(21) Appl. No.: 10/245,115

(22) Filed: Sep. 17, 2002

(65) Prior Publication Data

US 2003/0059620 A1 Mar. 27, 2003

Related U.S. Application Data

(62) Division of application No. 09/415,943, filed on Oct. 8, 1999, now Pat. No. 6,500,549.
(60) Provisional application No. 60/104,001, filed on Oct. 13, 1998.

(51) Int. Cl.⁷ .............................................. B32B 25/20
(52) U.S. Cl. .................. 428/425.5; 525/447; 525/474; 525/464; 525/453; 428/411.1; 528/28; 528/59; 528/65
(58) Field of Search .................. 428/425.5, 411.1; 525/447, 474, 464, 453; 528/28, 59, 65

(56) References Cited

U.S. PATENT DOCUMENTS

| 3,582,423 A | 6/1971 | Wang ........................ 156/232 |
| 4,242,474 A | 12/1980 | Shinohara et al. .......... 525/404 |
| 4,861,830 A | 8/1989 | Ward, Jr. ..................... 525/92 |
| 4,945,148 A | 7/1990 | Rich et al. .................... 528/26 |
| 5,179,142 A | 1/1993 | Ono et al. .................... 524/35 |
| 5,266,645 A | 11/1993 | Siol et al. ................... 525/309 |
| 5,312,652 A | 5/1994 | Antoine ...................... 427/387 |
| 5,589,563 A | 12/1996 | Ward et al. ................... 528/44 |
| 5,702,823 A | 12/1997 | Forrestal et al. ............ 458/450 |
| 5,738,902 A | 4/1998 | Forrestal et al. ........... 427/2.12 |
| 5,863,627 A | 1/1999 | Szycher et al. ............. 428/36.8 |

FOREIGN PATENT DOCUMENTS

| EP | 0 386 547 A3 | 12/1990 | ......... C08G/77/448 |

OTHER PUBLICATIONS

Costerton, JW et al. (1999), "Bacterial Biofilms: A Common Cause of Presistent Infections;" *Science* 284:1318–1322.

Deppisch, R et al. (1998), "Microdomain Structure of Polymeric Surfaces—Potential for Improving Blood Treatment Procecures;" *Nephrol. Dial. Transdplant* 13:1354–1359.

Tezuka, Y et al. (1991), "Environmentally Induced Macromolecular Rearrangement on the Surface of Polyurethane–Polysiloxane Block Copolymers;" *J. Chem. Soc.* 87(1):147–152.

*Primary Examiner*—Kuo-Liang Peng
(74) *Attorney, Agent, or Firm*—Greenlee, Winner and Sullivan, P.C.

(57) ABSTRACT

The present invention includes a co-polymer film which can be applied over a surface of an article to form a continuous surface that is more biocompatible and has a smoother surface morphology than an untreated article. In general the co-polymer film of the invention can be formed by providing a hydrophobic polymer block, such as polydimethylsiloxane (PDMS) with functional —OH end groups and reacting the —OH ends with a conventional monomer or prepolymer of a film-forming polymer capable of reacting with —OH groups. Such reactions are exemplified, using as reactive PDMS a triblock copolymer of the polylactone-polysiloxane-polylactone (PL-PDMS-PL) type, or silicone polyesters. The —OH groups of the polylactone blocks can react with any of a variety of isocyanates in a suitable solvent to form a polymer having PDMS incorporated with its structure. The film can be applied to the surface of an article by any convenient means of coating the article with the reaction mixture in solvent, and allowing the solvent to evaporate.

16 Claims, 4 Drawing Sheets

PUR (1 comp)

PUR (1 comp) with SMA

PUR (2 comp)

PUR (2 comp) with SMA

BIOCOMPATIBLE POLYMER FILM

CROSS REFERENCE TO RELATED APPLICATIONS

This application is a divisional application of U.S. patent application Ser. No. 09/415,943 filed Oct. 8, 1999, now U.S. Pat. No. 6,500,549, which claims priority from U.S. Provisional Application No. 60/104,001 filed Oct. 13, 1998.

BACKGROUND OF THE INVENTION

The present invention relates to the basic problem that many of the biomedical devices used in contact with live tissue or body fluids are made of materials of synthetic or natural origin which are not biocompatible. Lack of biocompatibility can lead to blood clotting as well as various other manifestations of inflammation and tissue activation.

In addition, microbial infection can establish themselves on device surfaces. Infectious agents such as bacteria that colonize and form biofilms on surfaces can prove exceedingly difficult to eradicate, [Costerton, J. W. et al. (1999) *Science* 284:1318–1322]. Devices intended for long-term contact such as implanted stents or indwelling catheters can also serve as a surface for host cell adhesion, permitting host cells to become activated, proliferate or to alter normal physiological function and to restrict function or intended use of a device, for example by restricting fluid flow through the device.

An approach used in the prior art to improve biocompatibility has been based on modifying the surface of a device to make it more hydrophobic. On the other hand increased biocompatibility at least in part can be achieved by making a surface more hydrophilic. Although certain types of polymers, such as silicones and siloxanes, are known to possess many attributes of biocompatibility, there are no reliable physical correlates which enable one to predict biocompatibility with any degree of certainty. Generally, hydrophobic surfaces are more biocompatible than hydrophilic surfaces. Zisman's critical surface tension [Zisman, W. A., (1964) *Adv. Chem: Ser.* 43] has been used as a parameter to help assess potential biocompatibility. Materials with an optimum critical surface tension are frequently biocompatible, yet there are notable exceptions. For example, polyethylene and polypropylene have critical surface tensions well within the optimum range, but they are not predictably biocompatible. Other factors are also important. Without a clear understanding of the nature of these factors, biocompatibility remains unpredictable.

Because of the attractive structural properties of polyolefins and polyurethanes, various blending and copolymerization techniques have been developed to impart greater biocompatibility. U.S. Pat. No. 4,872,867 discloses modifying a polyurethane with a water soluble polymer and crossing them in situ with a silane-type coupling agent to form a cross-linked and intertwined polysiloxane network. U.S. Pat. No. 4,636,552 discloses a polydimethyl siloxane with polylactone side chains which are said to be useful for imparting biocompatibility when combined with a base polymer, or used to replace plasticizer. U.S. Pat. No. 4,929,510 discloses a diblock copolymer having a more hydrophobic block and a less hydrophobic block. A solution of the diblock copolymer in a solvent which swells the matrix polymer is used to introduce the diblock into an article of matrix polymer. Thereafter, the article is transferred to water, to force orientation of the incorporated diblock copolymer such that the more hydrophobic block is embedded in the matrix and the less hydrophobic block is exposed on the surface of the article. Examples of diblock copolymers included poly (ethyleneoxide-propylene oxide), N-vinyl-pyrrolidone-vinyl acetate and N-vinyl-pyrrolidone-styrene. U.S. Pat. Nos. 4,663,413 and 4,675,361 disclose segmented block copolymers, in particular polysiloxane-polycaprolactone linear block copolymers. The latter were incorporated into base polymer material to modify the surface properties thereof. Although initially blended in bulk into the base polymer, the copolymer migrates to the surface to form an exceptionally thin, possibly a monolayer film which imparts the desired surface characteristic, specifically, biocompatibility.

Triblock copolymers having a polydimethyl siloxane (PDMS) block flanked by polylactone (PL) blocks have been described, Lovinger, A. J. et al. (1993) *J. Polymer Sci. Part B.* (*Polymer Physics*) 31:115–123. Such triblock copolymers have been incorporated into bulk formulations, and also applied as surface coatings, to reduce thrombogenicity, as described in U.S. Pat. No. 5,702,823, incorporated herein by reference. PL-PDMS-PL triblock copolymers are commercially available, for example from Thoratec Laboratories, Berkeley, Calif., which provides a series of such polymers designated "SMA" in which the siloxane is dimethyl siloxane and the lactone is caprolactone, and also from Th. Goldschmidt A G, Essen Germany, under the name "Tegomer" (Trademark, Goldschmidt A G). The nominal molecular weights (number average) of the polysiloxane blocks suitable for use herein range from about 1000 to about 5000, while the nominal molecular weights of the caprolactone blocks range from about 1000 to about 10,000. Tsai, C-C. et al (1994) *ASAIO Journal* 40:M619-M824, reported comparative studies with PL-PDMS-PL blended into polyvinyl chloride and other base polymers or applied as a coating thereon.

Deppisch, R. et al. (1998) *Nephrol. Dial. Transplant.* 13:1354–1359 reported improved thrombogenic properties for films or membrane structures of polyamide-polyvinylpyrrolidone, polyamide-polyarylethersulfone-polyvinylpyrrolidone or polyarylether-polyvinylpyrrolidone. Improved thrombogenic properties were attributed to a microdomain surface structure of hydrophobic and hydrophilic surface patches.

U.S. Pat. No. 5,589,563 discloses polymers having surface-modifying end groups, for example, polyurethanes having hard segments and soft segments covalently bonded to end groups such as PDMS or aromatic polycarbonates. The surface-modifying end groups tend to concentrate on the polymer surface to increase the surface hydrophobicity.

More recently, it has been recognized that the interactions between biological substances and man-made materials leading to clotting, inflammatory responses and microbial and host cell reactions are more complex processes in which the surface hydrophobicity of the man-made material is but one factor. Interactions between biological materials and foreign substances have been shown to include, at a minimum, molecular interactions with components of the complement system, with the kallikrein-kinin system, with the intrinsic pathway of coagulation initiation, with platelet and with other cellular components of blood including peripheral blood cells, e.g. monocytes and granulocytes.

In addition, microbial growth and host cell activation and/or proliferation on the polymer surface are problems with potentially serious consequences, especially for implanted or indwelling articles such as catheters and stents. The design of materials having improved biocompatibility must take such factors into account.

SUMMARY OF THE INVENTION

The invention includes a co-polymer film and method for improving the biocompatibility of any article of synthetic/polymeric, organic or metallic origin intended to contact blood, tissue or body fluids in the course of a medical treatment or procedure. Such articles include, without limitation, tubing, bags, catheters, stents, probes, feeding tubes, drainage lines, vascular grafts, artificial shunts and the like whether intended for long-term or short-term contact with blood, tissue or other body fluid or their plasma or corpuscular and cellular constituents. The co-polymer film of the invention provides reduced thrombogenicity, reduced bacterial growth and adhesion, reduced toxicity to host cells, and infiltration and seeding with inflammatory cells or host cells, when compared to articles or materials in conventional use or without the polymer film described.

DETAILED DESCRIPTION OF THE INVENTION

The present invention includes a co-polymer film which can be applied over a surface of an article to form a continuous surface that is more biocompatible and has a smoother surface morphology than an untreated article. In general the co-polymer film of the invention can be formed by providing a hydrophobic polymer block, such as polydimethylsiloxane (PDMS) with functional —OH end groups and reacting the —OH ends with a conventional monomer or prepolymer of a film-forming polymer capable of reacting with —OH groups. Such reactions are exemplified, using as reactive PDMS a triblock copolymer of the polylactone-polysiloxane-polylactone (PL-PDMS-PL) type, or silicone polyesters. The —OH groups of the polylactone blocks can react with any of a variety of isocyanates in a suitable solvent to form a polymer having PDMS incorporated with its structure. The film can be applied to the surface of an article by any convenient means of coating the article with the reaction mixture in solvent, and allowing the solvent to evaporate.

A polymeric film having PDMS blocks incorporated within the polymer forms over the coated surface. The resulting film is mechanically stronger than coatings of PL-PDMS-PL alone. The film integrity makes it possible to encase any structure made of any material compatible with solvents used to dissolve the starting materials. Materials can be chosen for their optimal mechanical properties, then an article made of the desired material can be encased in a polymeric film of the invention to render the article biocompatible. The polymeric films of the invention are further advantageous in that they can reduce surface roughness which may exist in the article. As an example, in polyurethane-based catheters, barium sulfate is added to provide x-ray contrast. The barium sulfate increases the surface roughness, which can degrade the biocompatibility, induce flow turbulence or enhance cellular or microbial deposits. The polymer film applied to the catheter surface not only increases the biocompatibility by changing the chemical composition of the surface, but also by reducing the roughness of the surface. Other types of surface roughness, such as are introduced during fabrication, e.g. by injection molding or by extrusion or by thermal processes during tip shaping or by mechanical manufacturing steps such as mechanical or LASER based hole drilling, can be reduced by applying a polymer film of the invention.

Without intending to be bound by a particular theory of operation, data is provided herewith demonstrating that the polymer film of the invention has surface characteristics that are consistent with current understanding regarding biocompatible surfaces. Such current understanding takes note of the fact that cells, proteins and other biological materials interact nonspecifically with surfaces in a variety of ways, including hydrophobic, hydrophilic, and ionic or electrostatic interactions, the binding often being of a cooperative nature. A review of such interactions is found in Deppisch, R. al. (1998) *Nephrol. Dial. Transplant* 13:1354–1359, which is incorporated herein by reference. The type of surface that provides the least opportunity for interaction is therefore considered to be one which presents a patchy surface with domains of varying character smaller than the corresponding interacting domains commonly found on proteins, cells and the like. The co-polymer films of the invention are characterized by a non-uniform surface having domains of varied properties. The characteristics associated with such domains include hydrophobic/hydrophilic, rough/smooth, hard/soft, and the like. Optimal sizes lie in the range from 0.1–100 nm of average diameter, although boundaries need not be regular or precisely delineated, domain size need not be uniform and domains outside the optimal range are functional. Surfaces having such optimal patchiness do not provide a sufficient contact area for any given surface trait to allow non-specific binding of biological materials. The surfaces of polymer-films of the present invention have been analyzed by atomic force microscopy (AFM). The results, presented herein, demonstrate that the exemplified such films possess a patchy surface with domains of varied hydrophobicity and hardness which have average diameters in the range 0.1–100 nm.

Also presented herewith are data demonstrating significantly increased biocompatibility of surfaces covered by a polymer film of the invention, compared to an uncoated surface.

The invention therefore includes a co-polymer film generated by reaction of a hydrophobic polymer block, for example a PDMS-containing block copolymer having reactive —OH groups, with a monomer or prepolymer of a film-forming polymer, for example, an isocyanate or isocyanate-polyol mixture. There are many ways of forming a co-polymer film according to the invention. Suitable hydrophobic polymer blocks include various siloxane polymers, fluoropolymers, polyethyleneglycol-polydimethylsiloxane copolymers, silicone polyesters, polyamides, polysulfones, polyarlyethersulfone, polycarbonates, polyolefins including cycloolefine-copolymers and the like. Basically all kinds of block-copolymers can be applied for coating films according to the described invention. Reactive end groups on the hydrophobic polymer block can be any sort of reactive group suitable for coupling the hydrophobic polymer block with monomer or prepolymer units of the film-forming polymer. Alternatively, coupling agents can be used to react with the hydrophobic block and then with monomer or prepolymer units of the film-forming polymer.

Examples of film-forming polymers include polyurethanes, polyolefins, polycarbonates, polyvinyl chlorides polyamides, polysulfones, polyarylethersulfones, cellulosic polymers, cycloolefin-copolymers and the like. Preferred are polyurethanes (PUR) which can be formed by reaction of isocyanate with a polyol. PL-PDMS-PL has —OH groups which allow it to be incorporated internally into a polyurethane by reaction with free isocyanate groups.

The invention also provides a method of coating an article with a polymer film, by applying the products of the described reaction in a solvent over the surface of the article and removing the solvent, whereby the film is formed as the solvent is removed.

The invention is exemplified by two types of polymer film; using a commercially available PL-PDMS-PL block copolymer such as SMA 422, SMA 423 or SMA 425 (Trademark, Thoratec Laboratories Corp., Berkeley, Calif.) or a silicone polyester such as Tegomer H-Si 6440 (Trademark, Th. Goldschmidt A. G., Essen, Germany) in either a one component reaction with a polyurethane prepolymer (Desmodur E22 or E23, Trademark, Bayer Corp.) or a two-component reaction with an isocyanate, PL-PDMS-PL block copolymer and a polyol. In both reactions, PL-PDMS-PL blocks react as bifunctional units that become incorporated internally in the PUR polymer chain.

The reaction conditions can be varied so as to control the proportion of hydrophobic blocks to polyurethane. A preferred molar ratio of OH/NCO endgroups is in the range of 0.1 to 10. Reaction conditions which tend to increase the proportion of the hydrophobic block also tend to increase the overall hydrophobicity of the resulting film, and to increase the average diameter of the hydrophobic patches.

As a further aspect of the invention, biocompatibility, particularly reduced cell toxicity, can be improved by providing an interlayer between the surface of the article and the coating film. The interlayer can be formed of a hydrophobic material having free —OH groups such as polyol or one that is also a component of the coating film, such as PL-PDMS-PL (also referred to by trade names herein as SMA or Tegomer). The interlayer, e.g. PL-PDMS-PL can be applied by painting or immersing the article to be coated in a solution of PL-PDMS-PL dissolved in a suitable solvent, for example methyl-isobutyl ketone, then allowing the solvent to evaporate. The process, termed pre-coating, yields a layer of PL-PDMS-PL which can subsequently be coated with a polymer film of the invention, such that the PL-PDMS-PL coating forms an interlayer between the surface of the article and the polymer coating. Formation of an interlayer can be advantageous for reducing cell toxicity of coated articles, such as catheters, especially where the catheter is made of a polyurethane base polymer having leachable isocyanates. Multilayered films can also be prepared to provide a composite of physical properties not available from a single-layer coating.

EXAMPLE 1

Step 1:
    25 g Methylisobutylketone
    1.5 g SMA 422 (Thoratec Corp.)
    Warm up to 40° C. under light stirring, approximately 5 min.
        SMA 422 is a triblock co-polymer of polycaprolactone-polydimethylsiloxane-polycaprolactone blocks having nominal molecular weights of 4000, 2000 and 4000 respectively.

Step 2:
    Add 23.5 g Desmodur E22 (Bayer Co.)
    Light stirring to avoid air bubble formation. Reaction can be carried out for up to two hours, in temperature range 0° C.–60° C.
    Degassing
        Desmodur E22 is a polyisocyanate prepolymer based on diphenyl methane diisocyanate. The —NCO content is 8.6% by weight. Equivalent weight is 488.

Step 3:
    (a) Casting a film in various thickness on glass plate with a casting knife with or without support foil, e.g. PE (Polyethylene or injection molded plates made from polyurethane); or
    (b) Film forming by transporting solution through catheter tubes (ID 1–3 mm or any other geometry). The polymerized film was then examined by scanning electron microscopy (see FIG. 1).

EXAMPLE 2

Step 1:
    0.45 g SMA 422
    23.7 g polyol (VP51 Bayer Co.)
    15.9 g isocyanate (Desmodur PF Bayer Co.)
    Isocyanate and SMA 422 were allowed to react together for up to 10 min. at 60° C. Polyol was then added and the reaction further carried out as in Example 1, Step 2.
    Mixing and degassing at room temperature.

Step 2:
    Casting as film (described above) or potting.

Other reactions of OH-groups on PL-PDMS-PL are well-known in the art and can be exploited for incorporating hydrophobic blocks into a film-forming polymer. The reaction for PL-PDMS-PL can be augmented by reaction with coupling reagents which can then react with functional groups present in other polymers or monomers. Coupling to monomers or prepolymers having —OH functional groups can be carried out using alkyl or aryl sulfonates, e.g. tosylchloride which can be reacted with the monomer or prepolymer, R—OH, then substituted by a OH-group of PL-PDMS-PL.

Monomers or prepolymers having an amine, thiol or alcohol functional group can be activated by cyanuric chloride, then coupled to PL-PDMS-PL. Monomers or prepolymers having an epoxy group can be reacted directly with the OH groups of PL-PDMS-PL. Other coupling agents include anhydrides such as maleic anhydride or maleic acid anhydride copolymer, active esters such as N-hydroxy succinimide and esters of carboxylic acids or carboxylic acids activated by various carbodiimides. In general, a wide variety of such coupling reactions is known in the art and can be exploited to incorporate hydrophobic blocks into film-forming polymers, using known reaction conditions.

EXAMPLE 3
Testing/Assessing Thrombogenicity

Films or coated catheter tubes were tested for thrombogenicity assessment using freshly donated human blood. During contact of blood components with the material the kinetic generation of thrombin-anti-thrombin III complex (TAT) was analyzed as an indicator of thrombin formation. Thrombin is the major component in the coagulation circuit, since thrombin is a potent activator for platelets and cleaves fibrinogen to fibrin, which finally leads to a polymerized network, i.e. a clot. TAT was measured by a commercially available ELISA test according to the instruction of the manufacturer (Behring Co., Germany). The comparison of materials/surfaces is done in direct comparison of the modified versus the non-modified polymer system. Accelerated reaction kinetics for TAT indicates less biocompatible, more thrombogenic material.

For details on methodology for thrombogenicity assessment: Deppisch R. et al. (1993) *Nephrol. Dial Transplant* Supp. 3 (1994)17–23 and Tsai et al. (1994) *ASAIO J.* 40:M619-M624

In vitro analysis was performed with freshly donated human whole blood. Similar results, i.e. reduction of TAT, was measured for Example 2—SMA in 2 component PUR.

TABLE I

TAT data for SMA-PUR coated tubes according to Example 1.

| Types<br>Blood contact time | TAT<br>(ug/ml)<br>t = 21 min | TAT<br>(ug/ml)<br>t = 42 min | TAT<br>(ug/ml)<br>t = 81 min | TAT<br>(ug/ml)<br>t = 81 min |
|---|---|---|---|---|
| Non-treated | 2 | 251 | 1570 | clot already formed |
| Treated (60% solvent/ 5% SMA, 35% E22) | 1 | 73 | 605 | 1313 |
| Treated (50% solvent/ 5% SMA, 45% E22) | 1 | 1 | 54 | 65 |

EXAMPLE 4
Si/PDMS Surface Concentration (XPS)

In order to assess the presence of Si, the central component in PDMS molecule x-ray fluorescence spectroscopy was applied. The technique used was described before, e.g. for PVC-SMA mixtures by Tsai et al. (1994) *ASAIO J.*, 40:M619-M624.

Results for films containing no or 3% SMA (related to isocyanate compound) were obtained for different take-off angles (TOA), i.e. 10, 45 and 90°. It is important to note the greater the take-off angle the higher is the penetration depth for the analysis.

TABLE II

| Types | Atom (%)<br>TOA 10° | Atom (%)<br>TOA 45° | Atom (%)<br>TOA 90° |
|---|---|---|---|
| Ex. 1 product non-treated | 0 | 0 | 0 |
| Ex. 1 product treated 3% SMA | 17.9 | 12.4 | 9.62 |

These data show that Si, due to the presence of PDMS-content in the SMA-PUR, increased with decreasing TOA which indicates enrichment of SMA-PUR when cast as described above. In the given example an approximate 20-fold enrichment was realized. This experiment demonstrates that enrichment of the PDMS occurs in the surface.

TABLE III

| Types | Atom (%)<br>TOA 10 | Atom (%)<br>TOA 45 | Atom (%)<br>TOA 90 |
|---|---|---|---|
| PUR 2 component non-treated | 0 | 0 | 0 |
| PUR 2 component treated (3% SMA) | 15.7 | 8.2 | 6.0 |

These data confirm the enrichment of SMA-PUR polymer chains to the uppermost surface.

EXAMPLE 5
Scanning Electron Microscopy (SEM)

Figure 1:
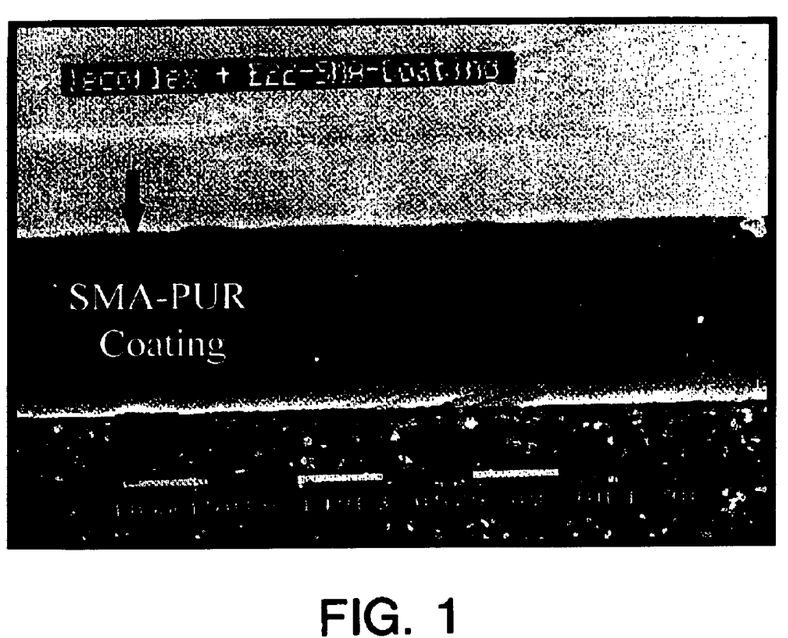
FIG. 1—Scanning electron microscopy of a catheter tube cross section having $BaSO_4$ incorporated into the catheter material for enhanced x-ray contrast. The interior, blood contacting surface is uppermost. The arrow designates a PUR-SMA film applied to the inner surface of the base material.
Figure 2A:
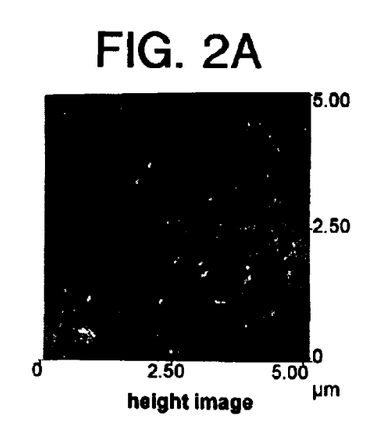
FIG. 2—Atomic force microscopy scans of single component PUR (top row) and PUR coated with a PUR-SMA film. Left row shows height variations, right row shows phase variations associated with drag on the probe tip. Light and dark areas have different physico-chemical characteristics, the light areas indicating a more soft and hydrophilic surface character, the dark areas indicating a surface that is relatively hard, hydrophobic and associated with a higher surface concentration of PDMS.
Figure 2B:
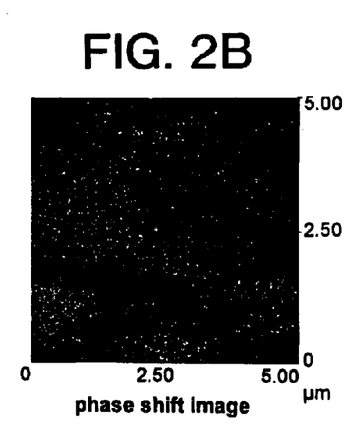
Figure 2C:
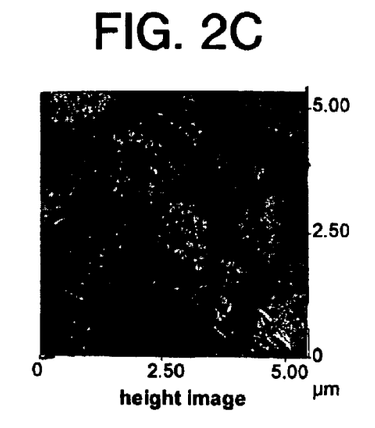
Figure 2D:
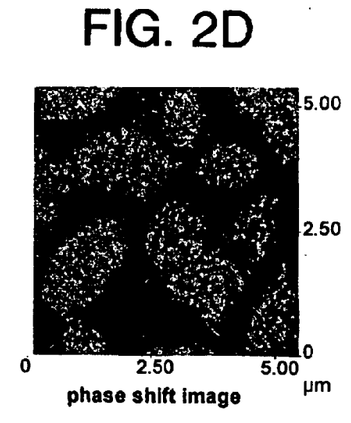
Figure 3A:
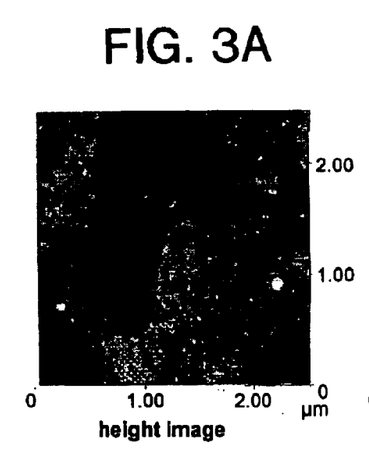
FIG. 3—Atomic force microscopy comparing surfaces of a two component PUR (top row) and a coating of 2 component PUR with SMA. Height and phase images, left and right respectively, are as described for FIG. 2.
Figure 3B:
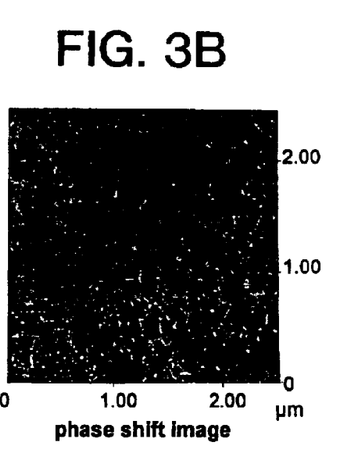
Figure 3C:
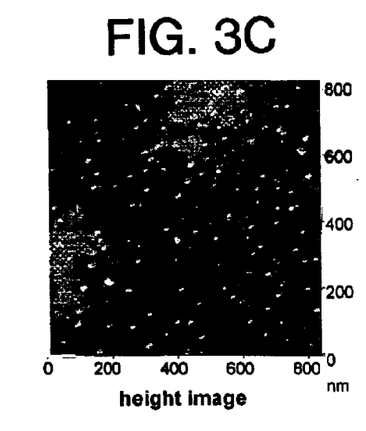
Figure 3D:
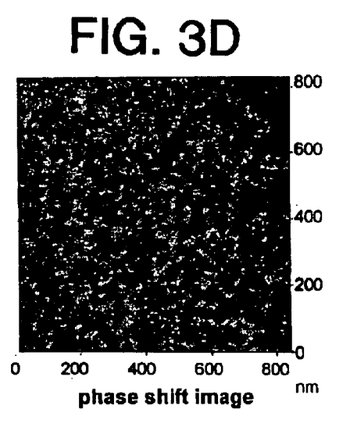

Non-modified and SMA-modified films on catheter tubes prepared as cross-cuts were sputter coated with a thin Pt/Au layer and analyzed in a Philips electron microscope. As shown in FIG. 1, a coating film of approximately 20 $\mu$m forms labeled "SMA-PUR coating." The coating process allows variation of the film thickness optimally from about 0.1 $\mu$m to several 100 $\mu$m. Furthermore, SEM also identifies small white spots which are due to the addition of $BaSO_4$ into the catheter material. $BaSO_4$ gives a change in emission of electrons in SEM. FIG. 1 shows a clear separation of the $BaSO_4$ from the blood contacting surface. As a conclusion: coated, blood-contacting surface lacks roughness due to $BaSO_4$ crystals, there is no release of $BaSO_4$ into blood, instead $BaSO_4$ remains in the catheter material.

EXAMPLE 6
AFM Pictures in Tapping Mode

The next issue in analysis was the confirmation of hypothesized nano-domains. Atomic force microscopy (AFM) is the most powerful technique to analyze nano-structures consisting of patches with different chemical or physicochemical properties.

The AFM analysis was performed applying tapping mode technique with low forces on the tip of the cantilever (reference for methods: Magonov et al. (1996) in *Surface Analysis with STM and AFM*, VCH, Weinheim), see FIG. 2 and FIG. 3.

The pictures of the surfaces taken or generated by AFM in tapping show different spots in the size of nanometers (10–100 nm in diameter). The picture defined as height image shows a kind of depth profile, whereas the picture defined as phase shift image shows the phase shift when the cantilever or tip is 'scratching' or moving on the surfaces (e.g. due to chemical forces or different softness). Light areas are more soft and hydrophilic. Darker areas have higher PDMS and are harder. By varying the molecular weight or chain length of the coating polymers, the person of ordinary skill in the art can readily modify the lateral structure of the nanodomain morphology.

EXAMPLE 7
Bacterial Adhesion

Evaluation of bacterial adhesion to co-polymer films and coated test plates was conducted by the method of Bechert, T. et al. (1998), XIth Aachen Colloquium on Biomaterials, Poster 26., German Offenlegung DE 19751581 A1. Adhesion of *Staphylococcus epidermis* on the material surface was quantified by means of photometry using an ELISA reaction to fix a dye to cells adhering on the surface of the material. Optical density measurements provide a relative quantitative measurement of adherent bacteria, under standardized conditions.

Various combinations of polyurethane (PUR) films, co-polymer films of PUR and PL-PDMS-PL, polyurethane test plates uncoated and coated with co-polymer films were tested.

Test plates were made of Tecoflex EG60DB20 (Thermedics, Inc., Woburn, Mass.) a thermoplastic, aliphatic polyurethane synthesized of methylene bis (cyclohexyl) diisocyanate (40%), polytetramethylene ether glycol (9.6%) and 1,4 diol chain extender (30.4%) with barium sulfate (20.0%) to impart x-ray opacity. Coating material was a one-component polyurethane essentially as in Example 1 formed from 35% Demodur E22, 5% PL-PDMS-PL (Tegomer) and 60% methyl isobutyl ketone (MIBK), cast as a film or coated on the Tecoflex test plates.

Test plates or films were exposed to a viable culture of S. epidermis for a period of 48 hours, with absorbance readings every twenty minutes.

Figure 4:
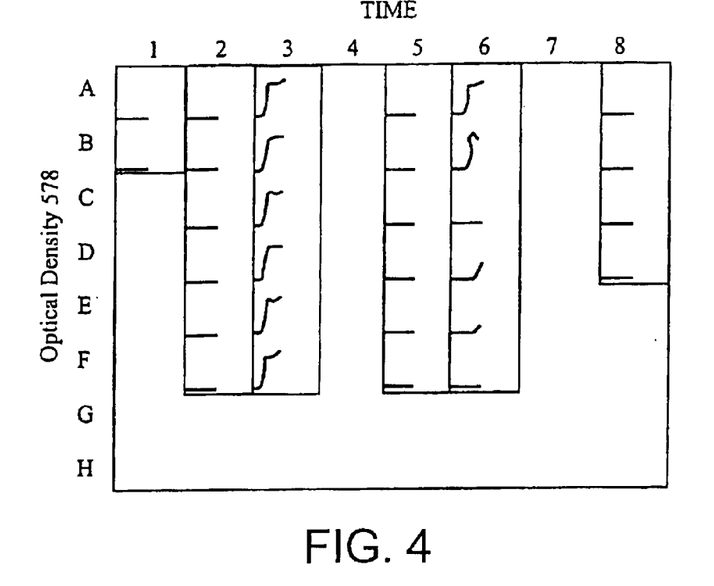
FIG. 4—Bacterial colonization of polyurethane test plates uncoated (row 3) and coated with PUR-PL-PDMS-PL film (row 2) and films of PUR (row 5) and Pul-PL-PDMS-PL coplymer (row 6). Horizontal axis:time (24 hrs. maximum); vertical axis, optical density at 578 nm. Letters along vertical axis identify separate test plates.

Results are shown in FIG. 4. Optical density is plotted on the vertical axis against time on the horizontal axis, for a series of test replicates A–F. Uncoated plates (row 3) rapidly and reproducibly supported increasing density of adherent bacteria. Coated plates over the same time interval did not support measurable bacterial adherence. Films formed of polyurethane alone did not support measurable adherence. Co-polymer films of PUR and PL-PDMS-PL significantly retarded the adherence of bacteria compared to uncoated test plates, by an average of about 30 hours for the same optical density. Surprisingly the presence of PDMS at the surface reduces in a dose-dependent manner the bacterial adhesion and proliferation.

EXAMPLE 8
Cell Toxicity Studies

The toxicity of various combinations of test plate materials, film coatings and film-coated test plates was evaluated by measuring inhibition of cell growth (ICG). ICG was measured by making aqueous eluates of the various test materials, then incubating growing mammalian cells in culture medium containing the eluate, then evaluating cell viability by neutral red uptake.

The ICG test was begun by seeding a 96-well tissue culture plate with 1500–2000 mouse fibroblast cells (strain L-929) previously grown to subconfluence for 48–72 h in complete Eagles MEM. The plates were incubated for 24 h at 37° C. The medium was then removed and test eluates were added. The test eluates were made by incubating test plates or films in distilled water (1 ml for each 10 $cm^2$ test material) at 70° C. for 24 h.

For each plate, 250 $\mu$l 0.4% Neutral red solution was mixed with 20 ml of complete Eagle's MEM. The eluate incubation medium was removed and 200 $\mu$l/well of neutral red containing medium was added. The plates were then incubated for 3 h at 37° C. The solution was then discarded, the plates rinsed with 200 $\mu$l PBS/well. After that, 200 $\mu$l/well of 50% (v/v) ethanol and 1% (v/v) acetic acid in distilled water was added. After a 10 min wait the absorbance at 540 nm of each well was measured. ICG % was calculated as $$\frac{A_k - A_T}{A_k} \times 100$$

where $A_T$=mean absorbance in test solution minus mean absorbance in blank, $A_k$=mean absorbance in control (no cells) minus mean absorbance in blank. The materials are deemed non-toxic if ICG is <30% as described by Wieslander et al. (1991) *Kidney International* 49:77–79.

The following materials were employed:
Completed Eagles MEM:
500 ml Eagles MEM
50 ml Fetal calf serum
5 ml 200 m ML-Glutamine
5 ml Non-Essential Amino Acid solution.
0.5 ml Gentamycin 50 mg/ml
PBS (10× stock solution):

| NaCl | 80 g |
|---|---|
| KCl | 2 g |
| $KH_2PO_4$ | 2 g |
| $Na_2HPO_4$ | 11 g | dissolve in $H_2O$ to 1000 ml final volume.

The stock solution is diluted 10-fold and pH adjusted to 7.2.

50% ethanol, 1% acetic acid solution:
500 ml ethanol (96%)
490 ml water
10 ml Glacial acetic acid
4% Neutral red stock solution:
4 g Neutral red (Merck No.1376)
100 ml distilled water
Diluted 10-fold with water prior to use.

In parallel experiments uncoated Tecoflex catheters and co-polymer films were non-toxic, i.e. ICG<30% compared to water or saline solution as reference. However, catheters and test plates coated with co-polymer films were toxic. Substituting Desmodur E23 for Desmodur E22 resulted in co-polymer films which were non-toxic as films and non-toxic when applied to a catheter or test plate. Desmodur E23 has 15%-NCO groups.

Figure 5:
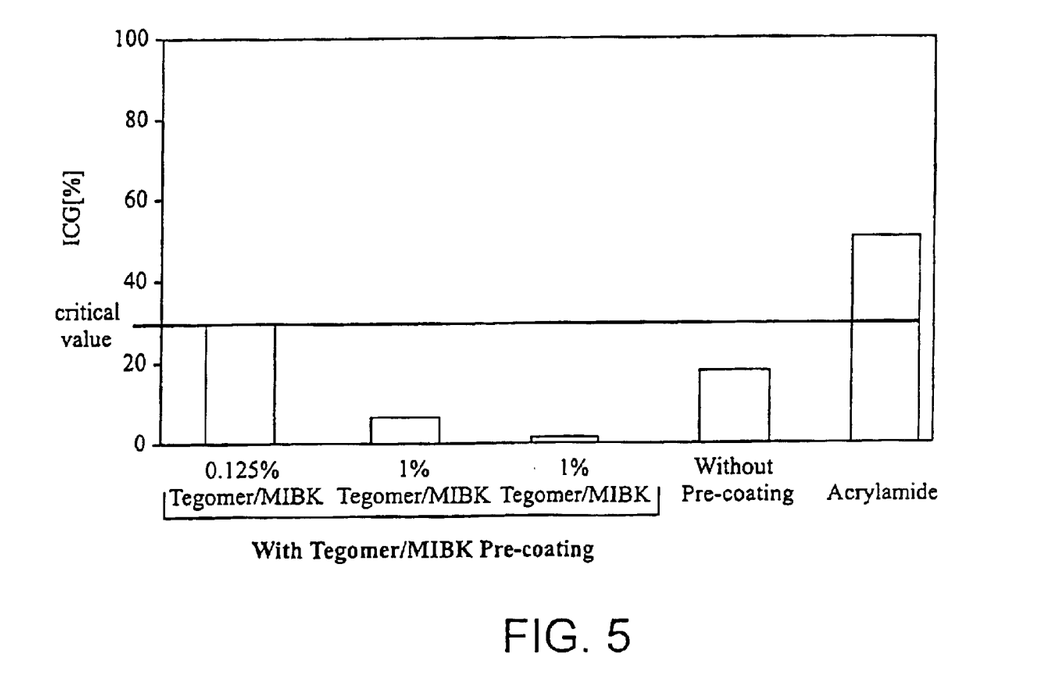
FIG. 5—Bar graph showing cell toxicity (inhibition of cell growth) of extracts of coated catheters with and without pre-coating as described below and in Example 8.

Toxicity was also reduced or eliminated by interposing an interlayer of polyol or PL-SMA-PL over the test material, prior to applying the co-polymer film. Test catheters were pre-coated with either 0.125% or 1.0% PL-PDMS-PL by applying the pre-coating in a solution of methyl-isobutyl ketone and curing at 40° C. to remove the solvent. Test catheters were then coated with co-polymer essentially as described in Example 1 except the co-polymer starting solution was 45% Desmodur E23, 5% PL-PDMS-PL and 50% MBK. The data are shown in FIG. 5. Catheters pre-coated with a PL-PDMS-PL interlayer had significantly reduced toxicity although catheters coated without an interlayer were also below the 30% ICG threshold for toxicity. Therefore, toxicity can be reduced either by interposing an interlayer having free-OH groups, or by employing rapidly reacting components to form the co-polymer film. Either strategy avoids or minimizes the possibility of reaction between the reaction components of the co-polymer film and the base polymer of which the article to be coated is formed. This multilayer concept as described above allows a great flexibility in composing the polymers.

EXAMPLE 9
Non-Attachment of Mammalian Cells

The failure of mammalian cells, such as fibroblasts, to attach and overgrow articles coated with a co-polymer film of the present invention was demonstrated in the following way: Fibroblast cells were inoculated on a tissue culture plate pre-coated on the bottom with a co-polymer film of the invention, a portion of which was overlaid by a glass plate with the entire apparatus bathed in growth medium. Growth on the co-polymer surface was compared to growth on the glass surface. Cells grew on the glass surface but failed to attach or proliferate on the co-polymer surface. The failure of cells to attach or proliferate on co-polymer film surfaces of the invention indicates that such surfaces are unlikely to be damaged when implanted, by ingrowth or overgrowth of host cell tissue.

The invention having been described by examples of specific embodiments of the operating principals of the invention, other embodiments will be recognized by those skilled in the art following the general teachings and principles taught or suggested herein. Those variations that fall within the scope of the invention include the use of alternative materials for forming the co-polymer films of the invention, alternative reaction conditions for film formation and/or coating, alternatives for interlayer formation or combinations thereof.

Summary of the Results:

The described SMA-PUR films show a series of improvements in terms of properties:
1. Mechanical stability of the film compared to a simple coating of PL-PDMS-PL;
2. Reduced roughness below 0.1 nm compared to technology used up to now;
3. Micro/Nano-domains in the range of 5–100 nm as proven by AFM:
4. Reduced thrombogenicity: lower TAT generation kinetics; and
5. Enrichment of PDMS to the surface as documented by ESCA and XPS analysis.

We claim:

1. A co-polymer film comprising a film-forming polymer component and a hydrophobic polymer block having reactive end groups, said film having a non-uniform surface characterized by domains of varied properties of hydrophobicity, roughness, hardness or other physico-chemically distinct patches, said domains having average diameters in the range 0.1 nm–100 nm, wherein the film-forming polymer is selected from the group consisting of polyurethanes, polyolefins, cellulosic polymers, polycarbonates, polyarylethersulfones, polysulfones, polyvinylchlorides, and polyamides, and the hydrophobic polymer block is selected from the group consisting of siloxane polymers, fluoropolymers, polyethyleneglycol-polydimethyl siloxane co-polymers, silicone polyesters and polylactone-polysiloxane-polylactone triblock co-polymers.

2. The co-polymer film of claim 1 wherein the film-forming polymer is a polyurethane and the hydrophobic polymer block is a polylactone-polysiloxane-polylactone triblock co-polymer.

3. The co-polymer film of claim 1 wherein the film-forming polymer is a polydiphenyl methane diisocyanate prepolymer and the hydrophobic block is a polycaprolacton-polydimethylsiloxane-polycaprolactone triblock co-polymer.

4. The film of claim 3 wherein prior to condensation, the proportion of —OH groups on the hydrophobic block to —NCO groups on the film-forming polymer is in the range of 0.1 to 10.0.

5. A method of making a co-polymer film comprising the steps of:
a) combining a film-forming polymer component and a hydrophobic polymer block having end groups reactive with the film-forming polymer component in the presence of a solvent such that all components are dissolved in the solvent, wherein the film-forming polymer is selected from the group consisting of polyurethanes, polyolefins, cellulosic polymers, polycarbonates, polyarylethersulfones, polysulfones, polyvinylchlorides, and polyamides, and the hydrophobic polymer block is selected from the group consisting of siloxane polymers, fluoropolymers, polyethylenealycol-polydimethyl siloxane co-polymers, silicone polyesters and polylactone-polysiloxane-polylactone triblock co-polymers;
(b) applying the components dissolved in the solvent to a surface to be coated; and
(c) forming a film over the surface to be coated under conditions that allow the solvent to evaporate and the components to react with one another,
whereby a co-polymer film having a non-uniform surface characterized by domains of varied properties of hydrophobicity, roughness, hardness or other physico-chemically distinct patches, and said domains having average diameters in the range 0.1 nm–100 nm, is obtained.

6. The method of claim 5 wherein the film-forming polymer component is a polyurethane-forming component and the hydrophobic block is a polylactone-polysiloxane-polylactone triblock co-polymer.

7. The method of claim 6 wherein, prior to reaction, the proportion of —OH groups on the hydrophobic block to —NCO groups on the film-forming polymer is in the range from 0.1 to 10.0.

8. A The method of claim 6 where in the film-forming polymer component consists essentially of a mixture of an isocyanate and a polyol.

9. The method of claim 5 wherein the step of applying the components dissolved in the solvent to a surface to be coated is carried out by immersing an article to be coated by the film in the solution, then removing the article to permit the solvent to evaporate.

10. The method of claim 5 wherein the surface to be coated has been pre-coated with a layer comprising a polyol, or a polylactone-polysiloxane-polylactdone triblock co-polymer.

11. A method of coating a surface with a biocompatible co-polymer film comprising the steps of:
(a) covering the surface with a solution comprising a film-forming polymer component and a hydrophobic polymer block component having end groups reactive with the film-forming polymer component, the components being dissolved in a solvent, wherein the film-forming polymer is selected from the group consisting of polyurethanes, polyolefins, cellulosic polymers, polycarbonates, polyarylethersulfones, polysulfones, polyvinylchlorides, and polyamides, and the hydrophobic polymer block is selected from the group consisting of siloxane polymers, fluoropolymers, polyethyleneglycol-polydimethyl siloxane co-polymers, silicone polyesters and polylactone-polysiloxane-polylactone triblock co-polymers; and
(b) removing the solvent from the solution covering the surface to allow the components react with one another, whereby a co-polymer film having a non-uniform surface characterized by domains of varied properties of hydrophobicity, roughness, hardness or other physico-chemically distinct patches, and said domains having average diameters in the range 0.1 nm–100 nm, is formed on the surface.

12. The method of claim 11 wherein the film-forming polymer component is a polyurethane-forming component and the hydrophobic block is a polylactone-polysiloxane-polylactone triblock co-polymer.

13. The method of claim 12 wherein prior to reaction, the proportion of —OH groups on the hydrophobic block to —NCO groups on the film-forming polymer is in the range from 0.1 to 10.0.

14. The method of claim 12 wherein the film-forming polymer component consists essentially of a mixture of an isocyanate and a polyol.

15. The method of claim 11 wherein the surface has been pre-coated with a layer comprising a polyol, or a polylactone-polysiloxane-polylactone triblock co-polymer.

16. The method of claim 15 comprising the added step of forming a film over the pre-coating, prior to forming the bio-compatible co-polymer film.

* * * * *

UNITED STATES PATENT AND TRADEMARK OFFICE
CERTIFICATE OF CORRECTION

PATENT NO.    : 6,841,255 B2
DATED         : January 11, 2005
INVENTOR(S)   : Deppisch et al.

It is certified that error appears in the above-identified patent and that said Letters Patent is hereby corrected as shown below:

Column 5,
Line 9, delete "polyarlyethersulfone" and replace with -- polyarylethersulfone --.

Column 11,
Line 49, delete "polyethylenealycol-polydimethyl siloxane" and replace with
-- polyethyleneglycol-polydimethyl siloxane --.

Column 12,
Line 39, delete "polylactone-polysiloxane-polylactdone triblock" with -- polylactone-polysiloxane-polylactone triblock --.

Signed and Sealed this

Twenty-sixth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,841,255 B2
DATED : January 11, 2005
INVENTOR(S) : Deppisch et al.

It is certified that error appears in the above-identified patent and that said Letters Patent is hereby corrected as shown below:

Column 5,
Line 9, delete "polyarlyethersulfone" and replace with -- polyarylethersulfone --.

Column 12,
Line 9, delete "polyethylenealycol-polydimethyl siloxane" and replace with
-- polyethyleneglycol-polydimethyl siloxane --.
Line 41, delete "polyalctone-polysiloxane-polylactdone triblock" with
-- polyalctone-polysiloxane-polylactone triblock This certificate supersedes Certificate of Correction issued April 26, 2005.

Signed and Sealed this

Thirtieth Day of August, 2005

JON W. DUDAS
*Director of the United States Patent and Trademark Office*